(12) United States Patent
Schurr et al.

(10) Patent No.: US 11,540,697 B2
(45) Date of Patent: Jan. 3, 2023

(54) TISSUE CLIP APPLICATION FITTING/RETROFITTING SET

(71) Applicant: OVESCO ENDOSCOPY AG, Tübingen (DE)

(72) Inventors: Marc Schurr, Tübingen (DE); Thomas Gottwald, Kochel am See (DE); Gunnar Anhöck, Reutlingen (DE); Franziska Baur, Nürtingen (DE); Sebastian Schostek, Tübingen (DE); Chi-Nghia Ho, Reutlingen (DE)

(73) Assignee: Ovesco Endoscopy AG

( * ) Notice: Subject to any disclaimer, the term of this patent is extended or adjusted under 35 U.S.C. 154(b) by 464 days.

(21) Appl. No.: 16/620,707

(22) PCT Filed: Jun. 12, 2018

(86) PCT No.: PCT/EP2018/065493
§ 371 (c)(1),
(2) Date: Dec. 9, 2019

(87) PCT Pub. No.: WO2018/229047
PCT Pub. Date: Dec. 20, 2018

(65) Prior Publication Data
US 2021/0052141 A1 Feb. 25, 2021

(30) Foreign Application Priority Data
Jun. 12, 2017 (DE) .......................... 102017112896.4

(51) Int. Cl.
*A61B 1/00* (2006.01)
*A61B 17/128* (2006.01)
(Continued)

(52) U.S. Cl.
CPC ...... *A61B 1/00087* (2013.01); *A61B 1/00089* (2013.01); *A61B 1/00101* (2013.01);
(Continued)

(58) Field of Classification Search
CPC ............ A61B 1/00098; A61B 1/00087; A61B 1/00101; A61B 17/1285; A61B 2017/00296
See application file for complete search history.

(56) References Cited

U.S. PATENT DOCUMENTS 9,295,470 B2   3/2016 Baur et al.
2008/0249542 A1 10/2008 Stokes et al.
(Continued)

FOREIGN PATENT DOCUMENTS

DE  202008007774 U1  8/2008
EP  2316350 A1  5/2011
(Continued)

OTHER PUBLICATIONS

German Search Report for German Application No. 10 2017 112 896.4, dated Apr. 16, 2018, 20 pages.
(Continued)

*Primary Examiner* — Matthew J Kasztejna
(74) *Attorney, Agent, or Firm* — RatnerPrestia

(57) ABSTRACT

A tissue clip application fitting set or retrofitting set includes a cap attachment for placement on the distal head of a medical endoscope, which has a placement section and a tissue clip holding section. The cap attachment is notched at least at two angular positions forming at least two notches/slots/grooves. A working channel leads into the hollow chamber and exits the hollow chamber radially in a region distal to the placement section and proximal to the radially supported tissue clip. A first guiding or leading element is arranged after the working channel belonging to the retrofitting set, as seen in the distal direction. A corresponding second guiding or leading element is arranged within the hollow chamber at an angular distance from the first guiding
(Continued)

or leading element so as to be oriented in extension to a working channel belonging to the endoscope.

10 Claims, 3 Drawing Sheets

(51) Int. Cl.
    *A61B 17/00*     (2006.01)
    *A61B 17/122*     (2006.01)

(52) U.S. Cl.
    CPC ........ *A61B 1/00137* (2013.01); *A61B 17/122* (2013.01); *A61B 17/1285* (2013.01); *A61B 2017/0023* (2013.01); *A61B 2017/00296* (2013.01)

(56) References Cited

U.S. PATENT DOCUMENTS

| | | |
|---|---|---|
| 2011/0190578 A1 | 8/2011 | Ho et al. |
| 2011/0208210 A1 | 8/2011 | Baur et al. |
| 2013/0325039 A1 | 12/2013 | Noda |
| 2014/0213847 A1 | 7/2014 | Green et al. |
| 2015/0182239 A1 | 7/2015 | Baker et al. |

FOREIGN PATENT DOCUMENTS

| | | |
|---|---|---|
| EP | 2596756 B1 | 2/2014 |
| JP | 2006158840 A | 6/2006 |
| JP | 2011120884 A | 6/2011 |
| WO | 2012174431 A1 | 12/2012 |
| WO | 2017070183 A1 | 4/2017 |

OTHER PUBLICATIONS

Hartmann, C., "Development and Testing of a Super-Elastic Clip System for the Treatment of Iatrogenic Colon Perforations After Caloscopy", Dissertation, Medical Faculty of the Eberhard Karls University to Tubingen, with English translation, 2007, 47 pages.
International Search Report and Written Opinion for International Application PCT/EP2018/065493, dated Sep. 19, 2018, 8 pages.
Japanese Notice of Reasons for Refusal for Japanese Application No. 2020-518579, dated Feb. 15, 2022, with translation, 25 pages.

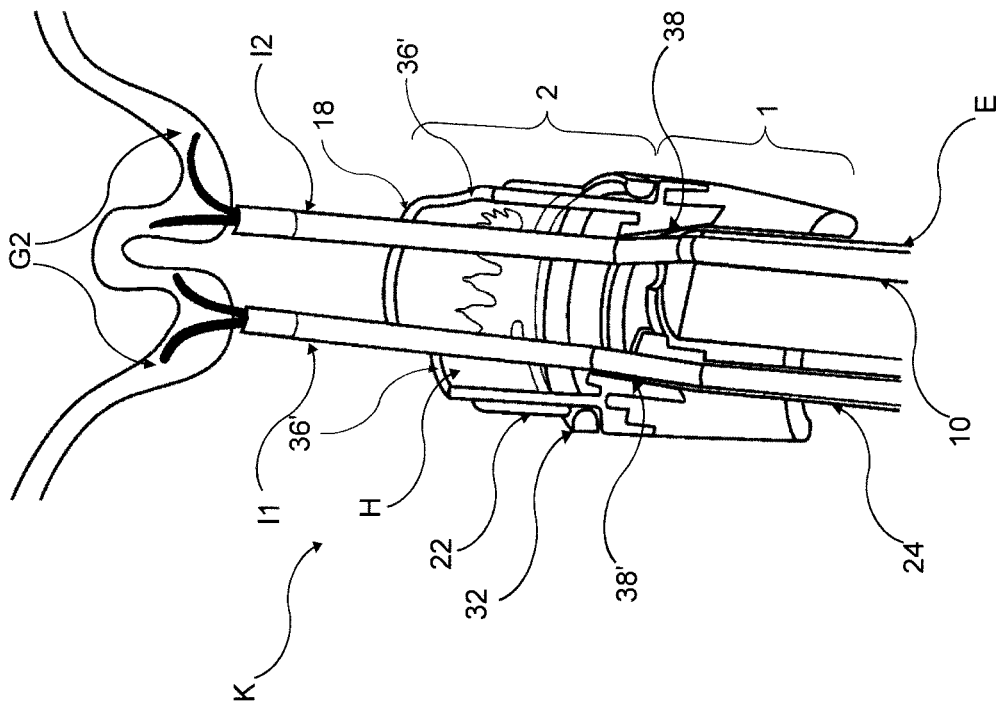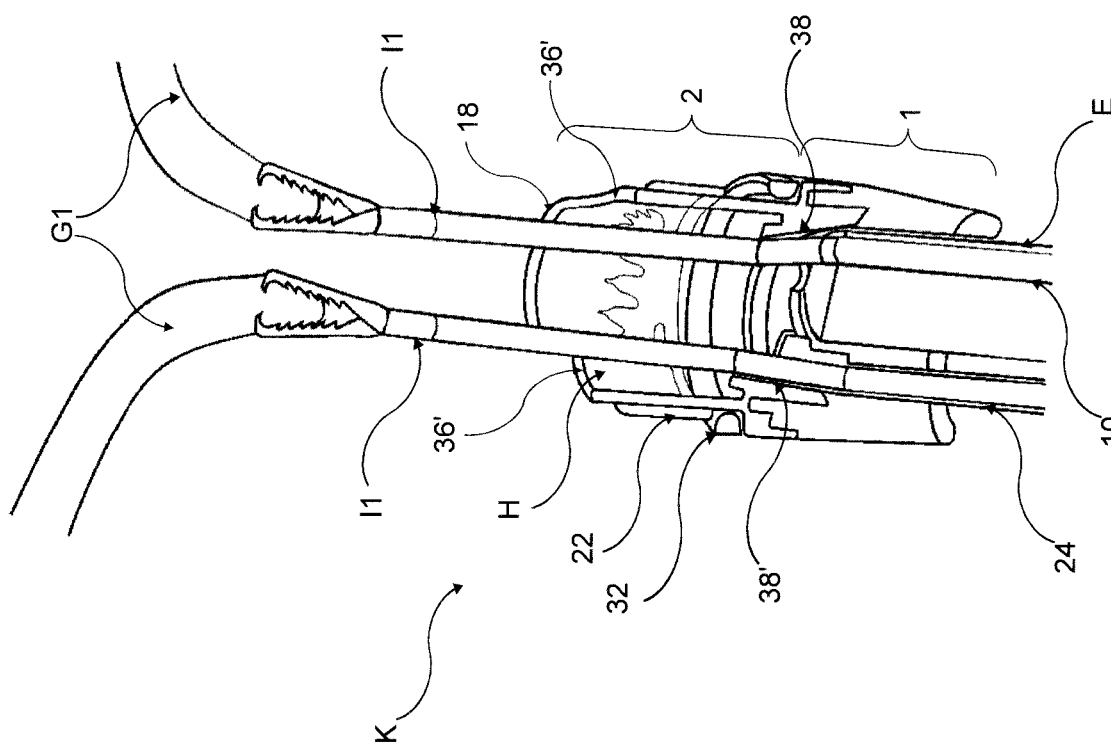

TISSUE CLIP APPLICATION FITTING/RETROFITTING SET

CROSS-REFERENCE TO RELATED APPLICATIONS

This application is the United States national phase entry of International Application No. PCT/EP2018/065493, filed Jun. 12, 2018, which claims the benefit of priority of German Application No. 10 2017 112 896.4, filed Jun. 12, 2017. The contents of International Application No. PCT/EP2018/065493 and German Application No. 10 2017 112 896.4 are incorporated by reference herein.

FIELD

The present invention relates to a tissue clip application set or retrofitting set, in particular a cap attachment for a medical endoscope.

BACKGROUND

Endoscopes are in general medical working appliances for the visual exploration and the possible manipulation of hollow chambers in a patient's body. They basically comprise optical devices at the distal end of the endoscope which faces the patient (also called endoscope head) and optionally one or a plurality of working channels extending from a proximal endoscope section (facing away from the patient) (which usually projects outwardly from the patient's hollow chamber) or from an extracorporeal endoscope grip through an (adjacent) flexible or rigid endoscope shaft to the endoscope head and enabling the extracorporeal introducing and supplying of one or a plurality of medical instruments, such as e.g. forceps, anchor, scissors, needle, loop, knife, and the like.

Such endoscopes may optionally be provided with additional capabilities, for instance, by attaching radially externally, at the distal endoscope end/endoscope head, a cap or sleeve on the endoscope head which accommodates/comprises at least the optics, said cap or sleeve being provided or equipped with particular functions/functional elements. Thus, the endoscope cannot only be used for the originally intended exploration and/or as an access for minimally invasive (medical) instruments, but can also be used itself as a (minimally invasive) instrument for performing an interventional or surgical process.

From the state of the art, for instance, of the applicant itself (e.g. DE 20 2008 007 774 U1), such a cap attachment is known which can optionally be placed radially externally on the head (distal end section in which at least one optics is placed) of a possibly generally known endoscope of the shaft type, and which carries, at a radial (outer) periphery, a tissue clip in the clamped state which can be introduced in the body hollow chamber of a patient. A clip pull-off means, for instance, a pulling thread (it may also be a pressure line, a push wire or a similar force transmission means) which cooperates with the tissue clip directly or indirectly, for instance, via a pusher or a piston and which can be operated from outside of the body hollow chamber, preferably on the grip of the endoscope so as to pull off the tissue clip from the cap attachment in a distal direction, is guided radially outside of the endoscope shaft or inside a working channel (if available) formed in the endoscope shaft.

This technology enables the fitting/retrofitting of a (standard) endoscope so as to turn it into a tissue clip application instrument.

Due to space restrictions and due to the hygienic necessity of designing such a cap attachment for an endoscope as a disposable product, the pulling thread or the push wire/pressure rod has prevailed over other, optionally usable actuation means (hydraulic, pneumatic, electromotive) as a force transmission means for pulling off the tissue clip. It is inexpensive, easy to guide and to handle, and reliable for pulling off/disengaging a tissue clip mounted in a clamped state on the jacket surface of the cap attachment. Normally, the pulling thread is, for instance, guided through the working channel within the endoscope shaft or through an additional channel mounted/mountable externally at the endoscope shaft to the proximal endoscope end section, reaches at the distal end of the endoscope through a radial bore spaced apart from the distal front edge of the cap attachment in an outward direction and is then guided back in the proximal direction to the tissue clip or to a pusher and/or pull off ring mounted directly behind the tissue clip.

In this place it is pointed out that the (known) cap attachment is, at least in the distal end section thereof, designed to be hollow inside such that tissue to be clamped can be pulled (partially) into the cap attachment, for instance, by the build-up of negative pressure (intake pressure) or by means of an instrument (gripping forceps/hook/anchor) guided through the working channel. Subsequently, only the thread has to be pulled to displace the tissue clip in a distal direction and to detach it from the cap attachment. The spreading energy stored in the clip is then released and the clip cramps the tissue section pulled into the cap attachment.

Since the cap attachment (adaptive placement cap) has to be conceived as a disposable product for hygienic reasons, the manufacturing costs have to be kept as low as possible. Therefore, the state of the art provides a simple cap shape with as few processing steps as possible for its manufacturing and as few movable components as possible, which may possibly restrict the usability of the known cap attachment.

Specifically, it has turned out difficult to seize and manipulate the patient's tissue to be treated in a correct and safe manner.

In the past, another problem turned out to be the normally circular cross-sectional shape of the cap attachment. If, in the case of a circular cross-sectional shape of the cap attachment and in particular in the case of a circular cross-sectional shape of its inner cavity which is open in the distal direction, patient's tissue to be clamped is sucked/pulled into the cap attachment/its cavity, the sucked patient's tissue is deformed (compressed) substantially circular-symmetrically. Especially in the case of a surgical incision by means of a scalpel or in electro surgery such a circular-symmetrical/circular deformation of the patient's tissue around the tissue cut is little meaningful since normally too much patient's tissue (alongside the tissue cut) has to be pulled into the cavity to clamp the surgical cut in its entire cutting length.

An oval cap shape would possibly be more favorable in this place, but this is more difficult to manufacture and cannot be coupled beneficially with an endoscope having a circular cross-section. Moreover, an oval shape is less suited for unproblematic (atraumatic) introduction into the patient's hollow chamber.

Finally, the applying of a tissue clip clamped/mounted at a circumferential outer side of a cap attachment is particularly difficult in the case of narrow hollow chambers of patients.

Modern medical endoscopes usually have a crooking section at the distal end section of their respective endoscope shaft. This is a bending-flexible shaft section of the endoscope which can optionally be cranked/bent actively (comparable to the finger of a human hand) by means of suitable force transmission means (Bowden cables, hydraulic means, etc.) from outside of the patient's hollow chamber via the endoscope shaft (passively bending-flexible or rigid) projecting at the end from the patient so as to turn, for instance, the endoscope head which is connected distally thereto in the proximal direction. Since the endoscope head is provided with optical means, the optics may in this manner be oriented actively laterally or even backward in the proximal direction.

If the crooking section is thus crooked actively with respect to the shaft longitudinal axis, the distal front side of the endoscope head may, for instance, be turned toward a hollow chamber wall (intestinal wall, esophagus wall, stomach wall, etc.) of the patient. If, however, a cap attachment in accordance with the foregoing description is attached additionally on the endoscope head, its axial length is quasi extended artificially in the distal direction, so that especially in narrow hollow chambers an active crooking of the crooking section belonging to the shaft may become problematic. In this respect, it would be of advantage to construct the cap attachment as short as possible, but it must be observed that the cavity formed in the cap attachment can still receive sufficient patient's tissue to ensure the safe applying of the tissue clip.

SUMMARY

In view of the afore-mentioned problems it is an object of the present invention to provide a generic cap attachment in accordance with the foregoing definition which features improved handling as compared to the state of the art known.

A preferred aim of the present invention is to construct the cap attachment such that also surgical incisions with a comparatively large cutting length can be clamped by the tissue clip without too much patient's tissue having to be pulled into the bowl-shaped cavity of the cap attachment.

Furthermore, it is a preferred aim of the present invention to facilitate altogether the applying of a tissue clip carried by the cap attachment.

Finally, it is an aim of the present invention to bring the constructional measures in the generic cap attachment which are necessary for achieving the afore-mentioned aims in line with the basic objective of being able to manufacture the cap attachment along with the clip pull-off means as a disposable product in an economically useful manner.

A gist or aspect of the present invention accordingly consists in notching the (adaptive) cap attachment (conceived as a retrofitting set) preferably in accordance with the foregoing definition, designed and provided for the (adaptive) placing on the radial outer circumference of an endoscope head (comprising optics) of a medical endoscope of the shaft type at its distal circumferential front edge formed in the distal transition from the inner cavity to an outwardly oriented peripheral surface/jacket surface of the cap attachment, at least at one angular position (by forming at least one notch/slot/groove intersecting the cap attachment in the axial direction/longitudinally), the cross-section of which may, for instance, be V- or U-shaped. The notch or else the axially extending recess may moreover extend over a particular partial circumference of the distal front edge, for instance, approximately one fourth or one third of the entire circumference of the distal front edge.

The so-produced notch/recess/gap (recessed in the axial direction) may comprise sharp-edged or rounded edges. It is also pointed out that the afore-mentioned outwardly oriented circumferential surface/jacket surface of the cap attachment on which the clip rests need not be the radially outermost jacket surface of the (substantially cylindrical) cap attachment which gets into contact with the patient's tissue, but may, for instance, be formed by an annular gap in the wall of the cap attachment or may be enclosed at least in sections and circumferentially by a further cylindrical wall or cover. In these latter-mentioned cases the tissue clip would be inserted in the annular gap from the distal in the proximal direction and would be covered/overlapped radially outwardly by the radially outermost wall portion.

Furthermore, in the present invention pursuant to the foregoing aspect at least two notches or at least two axially extending recesses are formed at the distal front edge of the cap attachment which preferably correspond to the construction of the afore-mentioned notch/recess. The two notches or axially extending recesses are arranged at a particular angular distance to each other, preferably diametrically opposed. Also, more than two notches/axially extending recesses may be provided at the distal front edge of the cap attachment, all of them having (substantially) the same cross-sectional shape, or being designed differently from each other. The notch depths (seen in axial direction) may also be equal to or different from each other. Finally, the notch base may extend in parallel or oblique to the distal front edge.

Irrespective of how many notches are provided, the at least two notches cause a pulling of the patient's tissue to be clamped into the inner cavity of the (cylindrical) cap attachment which deviates from a circular shape and is, for instance, oval or sickle-shaped even if the distal front edge is of circular shape (for instance, since the cap attachment is cylindrical).

In other words, it can be observed that, when the cap attachment is placed at the distal front end thereof (two-dimensionally/circularly) on a patient's tissue and the tissue enclosed (two-dimensionally) by the cap attachment is pulled into the inner cavity of the cap attachment by negative pressure or mechanically (e.g. by gripping forceps), it is deformed (during pulling), for instance, ovally (i.e. deviating from circular) by the at least one notch. In this manner, the tissue surrounding an incision (longitudinal cut) may, for instance, be pulled into the cavity and be clamped safely with minimal tissue surplus (alongside the cut).

In accordance with a further preferred aspect of the invention, the cap attachment is not fully cylindrical (or straight), but cranked and/or bent in a central section (by forming an angle preferably smaller than 90°, for instance, between 5° to 15° relative to the attachment longitudinal axis in the attachment longitudinal direction) such that at least the distal front edge of the cap attachment (in accordance with the foregoing definition), preferably said axial section in which the inner cavity is formed and further preferably said axial section on which the tissue clip is clamped/mounted, is bent relative to the attachment longitudinal axis (wherein in this case the distal front edge lies in a plane perpendicular to the bent section). In order to apply a tissue clip, the endoscope-side active crooking section which arranges itself proximally to the endoscope head and thus to the cap attachment has to be crooked much less actively for turning the distal front edge of the cap attachment toward the wall to be treated of the patient's hollow chamber.

In accordance with a further aspect of the present invention a longitudinal channel is arranged within the cap attachment and is preferably designed integrally with the cap attachment or is firmly connected to the cap attachment and exits laterally, i.e. radially outward at the jacket side of the cap attachment proximally to the tissue clip or the pull-off direction thereof, in order to then extend alongside the endoscope shaft at the outer side thereof (preferably retained temporarily on the endoscope shaft by clips or bands). Through this longitudinal channel, for instance, a surgical instrument such as gripping forceps may be advanced into the inner cavity, or a negative pressure (relative to the atmosphere) may be generated in the inner hollow chamber (inner cavity) through the longitudinal channel.

It is thus rendered possible to introduce, both through the at least one working channel of the (standard) endoscope and through the additional further working channel of the cap attachment (separate to the endoscope working channel), a respective medical instrument, for instance, for the gripping or holding of patient's tissue, into the inner cavity of the cap attachment and to thus pull the patient's tissue to be treated into the inner cavity simultaneously at two gripping points spaced apart from each other. Preferably, the additional working channel belonging to the cap attachment opens in the region of/in the longitudinal direction to the at least one notch, so that the patient's tissue can be pulled into the inner hollow chamber of the cap attachment safely via the at least one notch and/or recess(es) extending in the axial direction.

In accordance with a further aspect of the present invention, the cap attachment in accordance with the invention is provided with a preferably ramp-shaped deflector or deflection element, which is preferably formed integrally in the inner hollow chamber of the cap attachment and extends in the axial direction. The deflector and/or the deflection element is, seen in the distal direction, additionally oriented radially inwardly. It may further form a kind of chute or channel in which, for instance, a medical instrument can be guided longitudinally.

If the cap attachment is placed on the distal end of an endoscope (i.e. on the endoscope head), the cap attachment may be rotated on the endoscope head until the deflector and/or the deflection element is oriented to the opening of the endoscope-internal working channel in the axial direction (and forms quasi an extension of the working channel belonging to the endoscope). If a medical instrument is thus advanced through the working channel belonging to the endoscope into the inner hollow chamber of the cap attachment, the distal end section of the medical instrument experiences a (slight) guided deflection to the center of the hollow chamber from the deflector belonging to the cap. Thus, the patient's tissue can be gripped more centrally and can thus be pulled better and safer into the inner hollow chamber of the attachment cap.

Preferably, the cap-internal, additional working channel is also inclined toward the center of the hollow chamber seen in the axial direction.

According to a further aspect of the invention a further deflector and/or deflection element with the foregoing construction and function is designed/arranged distally to the opening of the cap-internal additional working channel.

Furthermore (especially in the case of a cranked cap attachment) an additional optical element such as, for instance, a mirror, may be arranged or designed at the inner wall of the cap attachment in order to extend the view starting out from the endoscope head and/or its optics in the direction to the distal front edge of the attachment, and/or the cap attachment is at least in sections formed of a transparent material so as not to or only slightly hinder the view in the distal direction by the bending. Finally, it is, however, also possible to equip the cap attachment with its own optics (separately/additionally to the endoscope optics available as a standard). Basically, at least the illumination of the endoscope may also be used further, wherein it is, of course, also conceivable to equip the cap attachment with its own light source in addition to the endoscope-internal illumination, so that the cap attachment in accordance with the invention can be used autarchically independently of the equipment of the (standard) endoscope.

In this place it is pointed out that from the state of the art, in particular also from the applicant's state of the art, application instruments are known (do not comprise optics and do thus not constitute endoscopes pursuant to the general definition, either) whose (rigid) instrument shaft is cranked/bent once or in an S-shaped manner directly before the instrument head (distal instrument end section) so as to turn the distal front side of the instrument head toward the wall of a patient's hollow chamber. In the present case, however, it is not the endoscope head and/or the shaft directly before (proximally to) the endoscope head that is cranked (which could be enabled by means of the actively actuatable crooking section). Rather, the cap attachment carrying the clip, which is arranged axially (in the distal direction) after the endoscope head and its optics accommodated therein, may preferably be cranked. Specifically, the crooking of the cap attachment takes place in an axial region which is distally spaced apart from a mounting/placement section (elastic bushing) of the cap attachment in the distal direction.

Thus, the endoscope shaft must, in the region of the bending section arranged directly before the endoscope head and thus the cap attachment, only be bent slightly (or not at all) actively to enable an exact applying of the tissue clip.

Finally, it is again pointed out explicitly that the aforementioned aspects (and their advantageous further developments) can be combined with each other at will where required.

Thus, for instance, the at least one front notch or a plurality of circumferentially spaced notches may not only be provided with the conventional cylindrical (rectilinear) cap attachment, but also with the cranked cap attachment. Also, the shape of the at least one notch is not restricted to a particular shape, but may be of any shape, such as, for instance, rectangular, triangular, trapezoidal, pitch circle-shaped, etc. A spike shape or a wave shape at the front edge of the cap attachment may also be provided.

The cranking may be in an angular range smaller than 90°, preferably between 5° and 15°.

The cap attachment is designed to support, at its jacket side, a tissue clip. Additionally, however, the cap attachment may also be equipped with its own tissue separating device, for instance, in the form of a laser or an electrical cutting loop, which is held/guided on the inner surface of the inner cavity and can be powered/actuated via a conductor strand guided in the endoscope shaft, preferably through the working channel thereof.

Finally, the cap attachment may additionally be designed with a kind of sleeve retainer which is firmly connected to the cap attachment (preferably material-integrally) and which (at least in sections) radially surrounds the tissue clip that is drawn onto a jacket surface.

Preferably, the peripheral/jacket surface oriented outwardly of the cap attachment (on which the tissue clip is directly mounted) may be designed with a longitudinal groove extending in axial extension to a radial bore guiding a pulling thread and provided for the axial/longitudinal guiding of the pulling thread emanating from the radial bore at the peripheral/jacket surface facing in outward direction. In this manner the pulling thread is, in the region of the jacket surface of the cap attachment, quasi sunk into the cap wall and can thus be traversed without hindrance by the tissue clip during the pull-off movement thereof.

As may be taken from the foregoing brief description, it is decisive for the success of the present invention, namely the specific deformation of the tissue pulled into the cap attachment for an optimized applying of the tissue clip, that the cap attachment comprises at its distal cap edge at least two preferably diametrically opposed notches or (longitudinal) slots, wherein the cap attachment is designed with its own working channel which preferably leads at a peripheral edge region of the cap attachment into the hollow chamber formed by the cap attachment for receiving the tissue pulled in.

Moreover, a deflector or a ramp (wedge) is formed in line with the two notches both downstream of the orifice position of the working channel belonging to the cap attachment and at a position which is preferably diametrically opposed, said deflector or ramp being adapted and provided to radially inwardly deflect a medical gripping instrument introduced through the working channel belonging to the cap attachment as well as a medical gripping instrument introduced simultaneously through the working channel of the endoscope, so that the two simultaneously introduced medical gripping instruments do not interfere with each other.

By the combination of these measures the intended deformation of the tissue pulled through the notches and gripped by the gripping instruments in the direct vicinity to the notches is achieved.

BRIEF DESCRIPTION OF THE DRAWING FIGURES

The invention will be explained in detail in the following by means of preferred embodiments with reference to the accompanying Figures.

FIG. 4A shows a first exemplary use of a tissue clip application fitting set or retrofitting set in accordance with the first preferred embodiment; and FIG. 4B shows a second exemplary use of a tissue clip application fitting set or retrofitting set in accordance with the first preferred embodiment.

DETAILED DESCRIPTION

Figure 1:
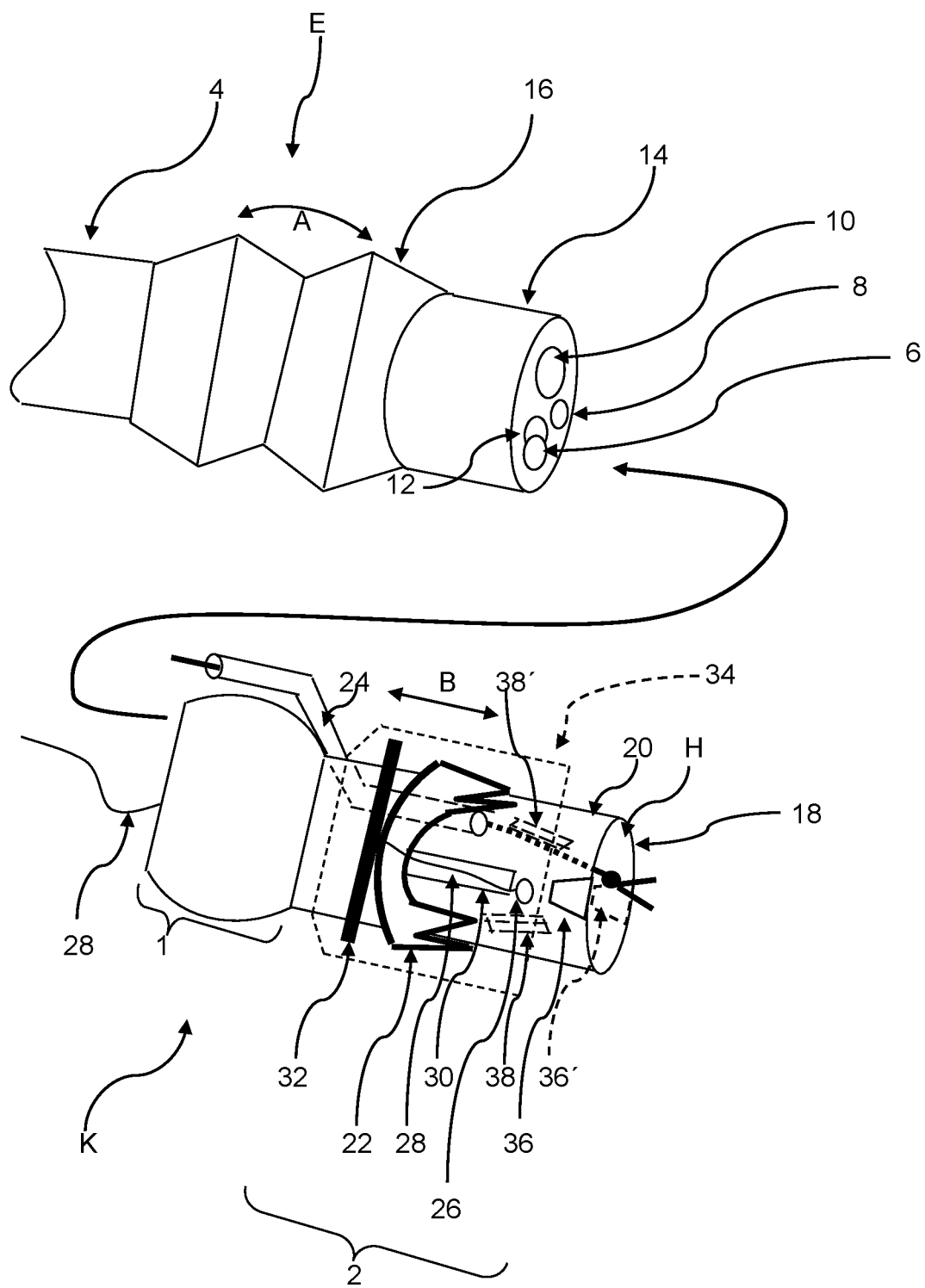
FIG. 1 shows a cap attachment in accordance with a first preferred embodiment of the present invention in preparation for being mounted on an endoscope head of a preferably generally known endoscope.

The tissue clip application fitting set or retrofitting set illustrated schematically in FIG. 1 has or consists of a cap attachment K comprising substantially a proximal placement section 1 and a distal tissue clip holding section 2.

The placement section 1 is designed in the form of a bushing or a collar of a flexible, preferably elastic material. Alternatively it is, however, also possible to manufacture the placement section 1 of a plastic sleeve which is radially expandable (e.g. by the arrangement of at least one longitudinal slot or due to a predetermined inherent flexibility). The placement section 1 is prepared for being placed on the distal end of a (commercially available) endoscope E preferably of known construction at the outer side thereof.

Normally, such an endoscope E has a (bending-flexible or rigid) endoscope shaft 4 at the distal end of which at least one optics 6 and one illumination device 8 are installed. Furthermore, an endoscope E of known construction has often an internal working channel 10 through which a medical instrument can be introduced into a patient's hollow organ, for instance. Finally, a rinsing device 12 may be provided at the distal end of the endoscope E, by means of which the optics 6 may be cleaned. In the following, the distal end section of the endoscope E, in which at least the optics 6 is accommodated, will be referred to as the endoscope head 14. An endoscope shaft section which can be crooked actively by an operator so as to orient the optics 6 toward the side or even in the proximal direction may optionally be arranged proximally before the endoscope head 14. This section will be referred to as the crooking section 16 of the endoscope E in the following.

The placement section 1 of the cap attachment K in accordance with the invention is now provided to be placed on the endoscope head 14 in accordance with the foregoing definition (not to be introduced into the endoscope working channel 6) so as to form quasi an axial extension of the endoscope head 14 and/or the distal end section of the endoscope shaft 4. The working channel 6 belonging to the endoscope thus remains open for the introduction of a medical instrument.

The tissue clip holding section 2 consists of a (hollow) plastic sleeve which is preferably more rigid relative to the placement section 1 and which is connected in extension to the placement section 1 integrally, preferably material-integrally, therewith, or is coupled to the placement section 1, for instance, by gluing or welding. The tissue clip holding section 2 forms at the inner side a cavity or a hollow chamber H which is provided to temporarily receive patient's tissue and which transitions, at the distal end of the tissue clip holding section 2, by forming a distal front edge 18, into a radial outer jacket surface 20 on which a tissue clip 22 is mounted in an axially movable manner (in the clamped state).

Inside the cap attachment K a working channel 24 is arranged or formed, which is formed (materially-) integrally with the cap attachment K or is firmly connected with the cap attachment and leads into the inner cavity/hollow chamber H in the distal direction. The working channel 24 belonging to the cap attachment (separately to the working channel 10 belonging to the endoscope) is guided radially to the outer side of the cap attachment K preferably in the region of the placement section 1 or distally thereof, so as to then extend over a predetermined length at least in correspondence with the length of the endoscope shaft 1 to be expected (approx. 2 m) such that the extracorporeal introduction of a minimally invasive medical instrument into the working channel 24 of the cap attachment K (separately to the normally available working channel of the endoscope) is possible.

In a distal end region of the cap attachment K a radial bore 26 is formed which connects the inner hollow chamber H with the jacket surface and through which a pulling thread 28 is guided. At the jacket surface/peripheral surface of the tissue clip holding section 2 which supports the tissue clip 22 radially, pursuant to FIG. 1 an axial groove 30 is formed which is open outwardly and which approaches the radial bore 28 in the axial direction Finally, at the jacket surface/peripheral surface of the tissue clip holding section 2 which supports the tissue clip 22 radially, a pull-off device with a pull-off ring/sliding ring 32 is mounted which is positioned directly proximally to the tissue clip 22 and to which the pulling thread 28 is coupled for an extracorporeally performed, preferably manual movement of the sliding ring 32 in the distal direction.

For this purpose, the pulling thread 28 is first of all guided through the axial groove 30 in the distal direction into the radial bore 26, deflected within the radial bore 26, and finally, for instance, guided back through the working channel 24 of the cap attachment K or the working channel 10 of the endoscope E or through a further separate channel in the proximal direction to the extracorporeal proximal end of the endoscope E.

As is finally indicated in FIG. 1 by dashed lines, the peripheral surface of the cap attachment K bearing the tissue clip may additionally be overlapped radially by a sleeve or an axially extending tongue 34 which covers the tissue clip 22 radially outwardly at least in sections.

In accordance with the first preferred embodiment of the present invention the distal front edge 18 comprises at least one notch and/or a first offset 36 extending in the axial direction. As is disclosed in FIG. 1, two notches/offsets 36, 36' may also be formed on the distal front edge 18 of the tissue clip holding section 2, which are preferably diametrically opposed. They may, however, also be positioned in any other angular distance to each other. Furthermore, the two notches preferably have the same shape and dimension. More than two notches may also be provided.

Finally, it is pointed out that the cap attachment K comprises, in the hollow chamber H thereof, at least a kind of guiding element (ramp) 38 which extends radially inwardly in the axial direction and seen in the distal direction. The guiding or leading element 38 is provided with a longitudinal groove or chute (illustrated in dashed lines) in which, for instance, a medical instrument may be guided longitudinally. If the cap attachment K in accordance with the invention is correctly mounted on the endoscope head, the guiding element 38 forms an axial extension to the working channel 10 of the endoscope E.

The cap attachment-internal working channel 24 may also be inclined radially inwardly seen in the distal direction and/or a further guiding element (ramp) 38' is arranged distally after the working channel 24 belonging to the cap attachment, said guiding element extending in the axial direction and simultaneously being inclined radially inwardly into the hollow chamber. Finally, each guiding element 38, 38' may be designed with a longitudinal groove or chute.

The function of the tissue clip application fitting set or retrofitting set pursuant to FIG. 1 can be described as follows:

First of all, the cap attachment K in accordance with the invention is placed on the head 14 of the (generally known) endoscope E at the outer circumferential side thereof. For the correct fit in the axial direction an inner axial stop, e.g. a radially inwardly directed circumferential annular projection or pinion (not illustrated) which will come to rest on the distal front side of the endoscope head 14 may be provided between the placement section 1 and the tissue clip holding section 2. Furthermore, the cap attachment K is rotated on the endoscope head 14 until the at least one guiding element 38 orientates itself in the axial direction to the exit opening of the working channel 10 belonging to the endoscope.

The working channel 24 belonging to the attachment is in the present example guided in the region of the placement section 1 or directly distally thereto radially outwardly from the hollow chamber H of the attachment K and extends externally along the preferably flexible endoscope shaft 4, 16 of the (generally known) endoscope E in the proximal direction to the outside of the patient's hollow organ to be treated As may be seen in FIG. 1, the endoscope E has the afore-mentioned crooking section 16 (also called crooking unit) between the head 14 and the shaft 4, which can actively be crooked optionally (in the direction of the Arrow A) from outside of the patient's hollow chamber/patient's hollow organ. In this way the endoscope head 14 may, along with the cap attachment K placed thereon, be oriented to face a hollow organ wall.

As soon as the cap attachment K has been pressed distally at the front side, i.e. with its distal front edge 18 (which is possibly rounded), against the tissue of the patient's hollow organ wall, the patient's tissue may be pulled into the inner cavity of the cap attachment K. This is done by means of negative pressure built up in the cavity and, for instance, generated through the working channel 24 belonging to the attachment, and/or by means of an instrument 24 (forceps, hook, tissue anchor, etc.) introduced through the working channel 24 belonging to the attachment. Additionally, a further medical instrument may be introduced into the hollow chamber H of the cap attachment K through the working channel 10 belonging to the endoscope so as to seize the patient's tissue to be treated at two spaced-apart positions and pull it into the cap-side hollow chamber H.

During the introduction of the medical instrument(s) into the hollow chamber H it/they slide(s) on the ramps 38, 38' and/or their longitudinal grooves and is/are thus pressed radially inwardly into the hollow chamber H. In this way the patient's tissue can be seized better. During the pulling of the patient's tissue into the hollow chamber H it is also pulled through the at least one notch 36, 36' and is deformed in this process. It has turned out that in particular in the case of an arrangement of at least one notch or better two notches 36, 36' in the region of the distal front edge 18 of the cap attachment K, which are, for instance, positioned diametrically to each other, the patient's tissue is no longer pulled into the cavity H circular-symmetrically, but rather ovally. Thus, a sufficient tissue mass can, for instance, be pulled into the attachment cap alongside a tissue cut without problems.

As soon as sufficient tissue has been pulled into the cavity H, the tissue clip 22 is, by means of the pulling thread 28, stripped off in the distal direction over the front edge 18 (along arrow B), and the tissue clip 22 then clamps the patient's tissue. In this process, the tissue clip 18 permanently travels over the pulling thread 28 without, however, interfering therewith since it is embedded in the axial groove 30.

Figure 2:
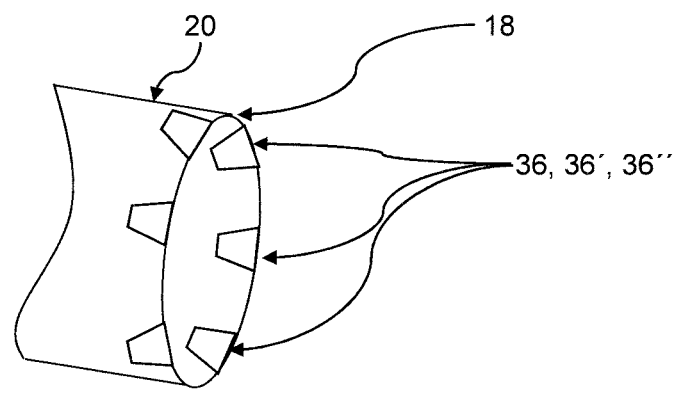
FIG. 2 shows a distal end section of the cap attachment in accordance with the invention pursuant to FIG. 1 with an alternative front edge shape.

In FIG. 2 a modification of the embodiment pursuant to FIG. 1 is illustrated.

In this case more than two notches 36 are formed at the distal front edge 18 of the cap attachment K in accordance with the invention, at least two notches of which are, for instance, positioned substantially diametrically to each other (not stringently necessary). All the further features of this modification correspond to those of the first embodiment pursuant to FIG. 1.

Figure 3:
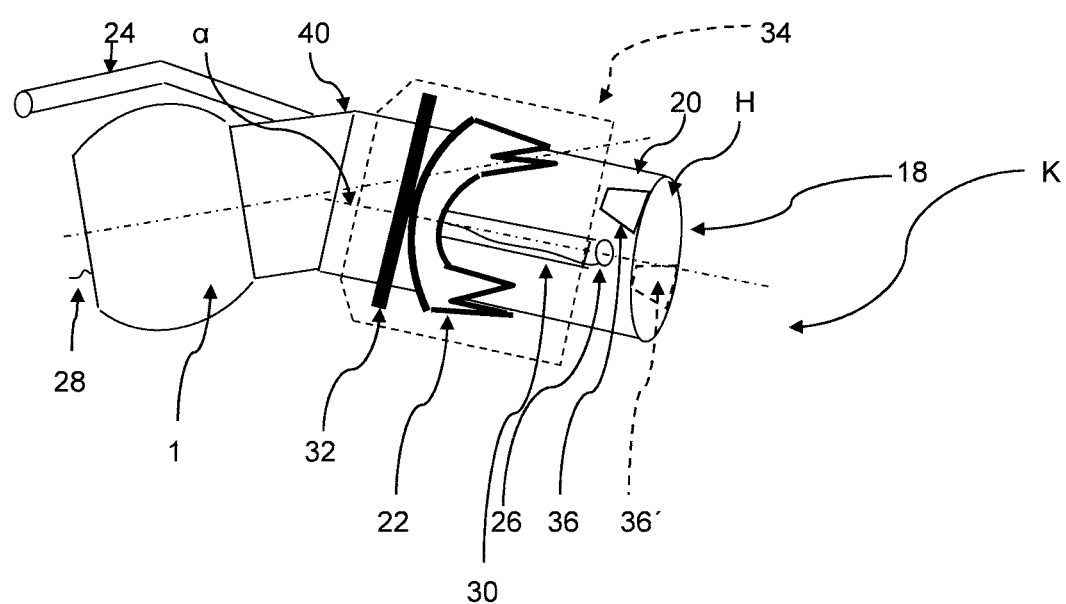
FIG. 3 shows a cap attachment in accordance with a second preferred embodiment of the present invention in preparation for being mounted on the endoscope head of the preferably generally known endoscope pursuant to FIG. 1.

FIG. 3 shows a second embodiment of the present invention. In the following, only those features will be described in detail in which the second embodiment differs from the first embodiment of the present invention. It is pointed out that the cap attachment K of the second embodiment may also be designed with distal notches 36 at the front edge 18 of the cap attachment and with a longitudinal groove 30 in accordance with the foregoing description, wherein these features have to be understood as mere optional features in the second embodiment. Moreover, guiding elements comparable to the first preferred embodiment may also be provided.

In contrast to the first embodiment the cap attachment K of the second embodiment is not straightly cylindrical, but cranked. In other words, the cap attachment comprises, in a central section which preferably separates the placement section 1 from the clip holding section 2, a kinking position/kinking edge 40 at which the cap attachment K is deflected/bent at an angle to the attachment longitudinal axis, i.e. deviates from the attachment longitudinal axis at an angle $\alpha$ preferably smaller than 90°, further preferred between 5° to 15°. The cranking position 40 is, for instance, proximal to the inner cavity H, i.e. for instance proximal to the pull-off ring/sliding ring 32.

In order to still guarantee the function of the endoscope E, on the head 14 of which the cap attachment K is placed pursuant to FIG. 3, in this case the cranking angle $\alpha$ is preferably chosen such that the field of view/direction of view of the optics 6 belonging to the endoscope and the illumination 8 thereof can only just detect the opening of the cavity belonging to the attachment. Moreover, endoscope-internal functions, such as e.g. the cleaning of the endoscope optics, are not influenced. Alternatively or additionally the cap attachment K is manufactured of a transparent material and/or means (not illustrated) are provided inside the cap attachment K which deflect/transfer the field of view/direction of view of the optics belonging to the endoscope and possibly the illumination thereof in the direction of the opening of the cavity. Alternatively or additionally the attachment K may, however, also be provided with its own optics (not illustrated).

The present invention relates in summary to a tissue clip application fitting set or retrofitting set with a cap attachment which is adapted to be placed on the distal head of a medical endoscope of the shaft type, and which comprises herefor a proximal placement section and a distal tissue clip holding section. In accordance with the invention the cap attachment may be cranked in a central section separating the placement section from the holding section by forming an angle $\alpha$ larger than 0° to the attachment longitudinal axis. Furthermore, the distal front edge of the cap attachment may be notched at least at one angle position forming at least one notch/slot/groove 28 intersecting the cap attachment in the axial direction.

FIGS. 4A and 4B illustrate by way of example two cases of use of a tissue clip application fitting set or retrofitting set in accordance with the first preferred embodiment to illustrate one of the problems underlying the invention. It consists in seizing and clamping safely and with a minimum of tissue damage two tissue layers G1 or tissue folds G2 which are separated from each other, wherein the tissue folds G2 first of all have to be produced by means of the tissue clip application fitting set or retrofitting set. This is, especially with the systems illustrated in the state of the art, not possible or only insufficiently possible.

FIG. 4A illustrates the use of the tissue clip application fitting set or retrofitting set in accordance with the invention during the treatment of an anastomotic insufficiency and/or a tissue perforation. Two or more tissue layers G1 which are separate from each other must be seized separately to subsequently connect them with each other/adapt them whilst they are pulled into the hollow chamber H of the cap attachment K, are folded in this process, and subsequently the tissue clip 2 is stripped off over them so as to clamp them together.

In order to be able to seize the tissue layers G1 separately, it is necessary to advance two separate surgical instruments I1, I2 (e.g. grippers or suction tubes) simultaneously through the hollow chamber in a directed manner to the patient's tissue H. For this purpose, two working channels 10, 24 are necessarily required to be able to introduce and actuate the two surgical instruments I1, I2 separately from each other. Furthermore, both surgical instruments I1, I2 must be deflected inwardly in a directed manner by means of the guiding elements/ramps 38, 38' so as to be each advanced in a directed manner to the tissue layers G1 where the instruments I1, I2 can precisely grip the individual tissue layers G1 at points spaced apart from each other. Subsequently the tissue layers G1 are pulled into the hollow chamber H of the cap attachment K by pulling the instruments I1, I2 back. Since the working channels 10, 24, the guiding elements/ramps 38, 38' and the notches/offsets 36, 36' are oriented axially to each other in the distal direction and/or are positioned in a plane extending through the longitudinal axis of the tissue clip holding section 2, the individual tissue layers G1 are placed in this process in the notches/offsets 36, 36', so that the tissue is folded. Then, the tissue clip 22 is stripped off the tissue clip holding section 2 and the tissue is thus connected/clamped.

FIG. 4B shows the use of the tissue clip application fitting set or retrofitting set in accordance with the invention in the case of a constriction of a hollow organ, for instance, a sleeve gastrectomy. For this purpose, two separate tissue folds G2 must first of all be produced. The proceeding corresponds substantially to that of the tissue treatment described before by means of FIG. 4A. For producing the two separate tissue folds G2 the directed advancing of the instruments I1, I2, and thus the deflecting of the instruments over the guiding elements/ramps 38, 38' is especially important so as to be able to grip two tissue points which are separate from each other and which are spaced apart from each other sufficiently for two separate tissue folds G2 to form when the instruments I1, I2 grip the tissue and pull it into the hollow chamber H. The tissue is folded through the notches/offsets 36, 36'. The tissue folds G2 so produced are placed on top of each other and clamped together by stripping off the tissue clip 22. In this way a relatively large amount of tissue can be diminished and thus the hollow organ can be distinctly constricted by just few clamping processes.

If the tissue were seized only at one single tissue point or at two tissue points which are very close together, it would not be possible to produce and clamp two separate tissue folds G2, or to clamp together two tissue layers G1 which are separate from each other.

The invention claimed is:

1. A tissue clip application fitting set or retrofitting set with a cap attachment which is adapted to be put over a distal head of a medical endoscope of the shaft type, the cap attachment comprising:
    proximal placement section;
    a cap section extending distally along an axial direction from the proximal placement section, the cap section comprising a sleeve-shaped circumferential wall that extends distally along the axial direction and comprises an inner surface and an outer peripheral surface spaced outwardly from the inner surface in a radial direction relative to the axial direction, wherein:

the outer peripheral surface comprises a tissue clip holding section configured to support a tissue clip in the radial direction, the inner surface forms an internal hollow chamber spaced radially inwardly from the outer peripheral surface, the internal hollow chamber at least partially overlaps the tissue clip holding section relative to the axial direction and the internal hollow chamber is open in the distal direction, and the circumferential wall terminates in the distal direction at a circumferential front edge that is connected at a radially inner side to the inner surface and is connected at a radially outer side to the outer peripheral surface, the circumferential front edge being intersected by at least two notches positioned at respective circumferential positions along the circumferential wall with each of the at least two notches extending along the axial direction in a proximal direction that is opposite the distal direction, and through the circumferential wall in the radial direction to form an opening in said circumferential wall, wherein the respective circumferential positions of each of the notches are spaced from each other in a circumferential direction of the circumferential wall;

a first working channel belonging to the tissue clip application fitting set or retrofitting set, the first working channel having a first working channel opening located inside the hollow chamber at a location along the axial direction between the placement section and the radially supported tissue clip, and wherein the working channel exits the hollow chamber at a location along the axial direction proximal to the radially supported tissue clip to thus be external to the endoscope;

a first guiding element arranged in the hollow chamber, wherein the first guiding element forms a first ramp portion that extends distally along the axial direction and radially inwardly away from the inner surface of the circumferential wall as the first ramp portion extends distally along the axial direction, wherein the first ramp portion is arranged distally along the axial direction from the first working channel opening, such that a first medical instrument introduced through first the working channel opening is deflected radially inwardly by the first ramp portion; and a second guiding element arranged within the hollow chamber wherein the second guiding element forms a second ramp portion that extends distally along the axial direction and radially inwardly away from the inner surface of the circumferential wall as the second ramp portion extends distally along the axial direction, wherein the second ramp portion is located distally along the axial direction from a second working channel belonging to the endoscope, such that a second medical instrument introduced into the hollow chamber from the second working channel is deflected radially inwardly by the second ramp portion, wherein the second ramp portion is spaced in the circumferential direction relative to the axial direction from the first ramp portion.

2. The tissue clip application fitting set or retrofitting set according to claim 1, wherein the first working channel opening is aligned along the axial direction with one of the notches.

3. The tissue clip application fitting set or retrofitting set according to claim 1, wherein the at least two notches are of U- or V-shaped design.

4. The tissue clip application fitting set or retrofitting set according to claim 1, wherein the cap section in a central section separating the proximal placement section from the tissue clip holding section is cranked or crooked relative to an attachment longitudinal axis along which the proximal placement section extends, forming an angle larger than 0° and smaller than 90°, such that at least the circumferential front edge of the cap attachment is bent relative to the attachment longitudinal axis.

5. The tissue clip application fitting set or retrofitting set according to claim 4, wherein the circumferential front edge is disposed in a plane which spans perpendicularly to a longitudinal axis of the at least a portion of the tissue clip holding section.

6. The tissue clip application fitting set or retrofitting set according to claim 4, wherein an axial region in which the hollow chamber is formed is bent relative to the attachment longitudinal axis.

7. The tissue clip application fitting set or retrofitting set according to claim 4, wherein a portion of the tissue clip holding section on which the tissue clip is supported radially is formed is bent relative to the attachment longitudinal axis.

8. The tissue clip application fitting set or retrofitting set according to claim 1, wherein the tissue clip holding section comprises a longitudinal groove which distally adjoins a radial bore in the tissue clip holding section which connects the hollow chamber with the outer peripheral surface, and extends in the axial direction toward the tissue clip.

9. The tissue clip application fitting set or retrofitting set according to claim 8, further comprising:

a pull-off means comprising a pull-off ring mounted in an axially sliding manner on the outer peripheral surface at a location directly proximally along the axial direction to the tissue clip, wherein the pull-off means comprises a pulling thread connected to the pull-off means, wherein the pulling thread extends into the longitudinal groove and through the radial bore to the hollow chamber, and is adapted to be run from the radial bore through the hollow chamber towards a proximal end of the hollow chamber and out of the hollow chamber.

10. The tissue clip application fitting set or retrofitting set according to claim 1, wherein at least one of the guiding elements forms a chute or a channel such that one of the medical instruments can be guided longitudinally therein.

* * * * *